United States Patent
Williams

(10) Patent No.: US 11,090,371 B1
(45) Date of Patent: Aug. 17, 2021

(54) TREATMENT OF CIRRHOSIS USING BOTULINUM TOXIN

(71) Applicant: PENLAND FOUNDATION, Beaumont, TX (US)

(72) Inventor: Roland M. Williams, Beaumont, TX (US)

(73) Assignee: PENLAND FOUNDATION, Beaumont, TX (US)

( * ) Notice: Subject to any disclaimer, the term of this patent is extended or adjusted under 35 U.S.C. 154(b) by 0 days.

(21) Appl. No.: 16/875,951

(22) Filed: May 15, 2020

Related U.S. Application Data

(63) Continuation-in-part of application No. 16/657,933, filed on Oct. 18, 2019, now Pat. No. 10,722,552, and a continuation-in-part of application No. 16/657,950, filed on Oct. 18, 2019, now abandoned.

(51) Int. Cl.
  *A61K 38/48* (2006.01)
  *A61K 9/00* (2006.01)

(52) U.S. Cl.
  CPC ........ *A61K 38/4893* (2013.01); *A61K 9/0019* (2013.01); *A61K 9/0021* (2013.01); *A61K 9/0085* (2013.01)

(58) Field of Classification Search
  None
  See application file for complete search history.

(56) References Cited

U.S. PATENT DOCUMENTS

| | | | |
|---|---|---|---|
| 5,766,605 | A | 6/1998 | Sanders et al. |
| 6,063,768 | A | 5/2000 | First |
| 6,139,845 | A | 10/2000 | Donovan |
| 6,632,440 | B1 | 10/2003 | Quinn et al. |
| 6,977,080 | B1 | 12/2005 | Donovan |
| 7,655,244 | B2 | 2/2010 | Blumenfeld |
| 8,734,810 | B2 | 5/2014 | Blumenfeld |
| 9,254,314 | B2 | 2/2016 | Finzi et al. |
| 9,707,207 | B2 | 7/2017 | Finegold |
| 10,011,823 | B2 | 7/2018 | Barbieri et al. |
| 10,258,673 | B2 | 4/2019 | Pokushalov et al. |
| 10,722,552 | B1 | 7/2020 | Williams |
| 2004/0062776 | A1 | 4/2004 | Voet |
| 2004/0220544 | A1 | 11/2004 | Heruth et al. |
| 2005/0147626 | A1 | 7/2005 | Blumenfeld |
| 2005/0191320 | A1 | 9/2005 | Turkel et al. |
| 2007/0259002 | A1 | 11/2007 | Batchelor |
| 2009/0142430 | A1 | 6/2009 | Sanders et al. |
| 2009/0232850 | A1 | 9/2009 | Manack et al. |
| 2010/0303788 | A1 | 12/2010 | Francis et al. |
| 2011/0200639 | A1 | 8/2011 | Blumenfeld |
| 2012/0093827 | A1 | 4/2012 | Van Schaack et al. |
| 2012/0195878 | A1 | 8/2012 | Haag-Molkenteller et al. |
| 2012/0244188 | A1 | 8/2012 | Blumenfeld et al. |
| 2012/0251519 | A1 | 10/2012 | Blumenfeld et al. |
| 2013/0251830 | A1 | 9/2013 | Manack et al. |
| 2015/0086533 | A1 | 3/2015 | Borodic |
| 2017/0173123 | A1 | 6/2017 | Blumenfeld |
| 2017/0333537 | A9 | 11/2017 | Borodic |
| 2018/0071361 | A1 | 3/2018 | Abiad et al. |
| 2019/0038646 | A1 | 2/2019 | Bright et al. |
| 2019/0300583 | A1 | 10/2019 | Jarpe |

FOREIGN PATENT DOCUMENTS

| | | | | |
|---|---|---|---|---|
| DE | 2072039 | * | 12/2007 | ............... A61K 8/64 |
| JP | 2012107051 | A | 6/2012 | |
| KR | 20100032982 | A | 3/2010 | |
| KR | 20150126979 | A | 11/2015 | |
| WO | WO 95/28171 | | 10/1995 | |
| WO | WO 00/10598 | | 3/2000 | |
| WO | WO 01/104058 | A | 2/2001 | |
| WO | WO 2005/072433 | * | 8/2005 | ......... A61K 38/4893 |
| WO | WO2010013495 | A1 | 2/2010 | |
| WO | WO2011084507 | A | 7/2011 | |
| WO | WO2014184746 | A | 11/2014 | |

OTHER PUBLICATIONS

Kumar, Asian J Pharm Clin Res, vol. 10, Issue 9, 2017, 21-29 (Year: 2017).*
Mortazavi et al., Ann Med Health Sci Res. Jul.-Aug. 2014; 4(4): 503-510. doi: 10.4103/2141-9248.139284: 10.4103/2141-9248.139284 (Year: 2014).*
The website downloaded Jul. 21, 2020 from Children's Hospital of Pittsburgh (https://www.chp.edu/our-services/transplant/liver/education/liver-disease-states/cirrhosis; 4 pages total (Year: 2020).*
Fernández-Rodriguez et al., Hepatology, 1995; 21: 35-40 (Year: 1995).*
The autonomic system schematic downloaded Nov. 23, 2020 from http://what-when-how.com/neuroscience/the-autonomic-nervous-system-integrative-systems-part-1/; the image is reproduced in the Office action (Year: 2020).*
Glatte et al., Frontiers in Neurology, 2019; 10: doi: 10.3389/fneur.2019.00970 (Year: 2019).*
Pugh KR et al, Abstract—"Glutamate and choline levels predict individual differences in reading ability in emergent readers", J.Neurosci. Mar. 12, 2014;34(11):4082-9. doi: 10.1523/JNEUROSCI.3907-13.2014 https://www.ncbi.nlm.nih.gov/pubmed/24623786 (Dec. 13, 2019).
Ryan J. Diel, MD et al, "Photophobia and sensations of dryness in migraine patients occur independent of baseline tear volume and improve following botulinum toxin A injections", HHS Public Access, Br J Ophthalmol. Author manuscript; available in PMC Aug. 1, 2019, pp. 1-15.

(Continued)

*Primary Examiner* — Christina M Borgeest
(74) *Attorney, Agent, or Firm* — Winston & Strawn LLP

(57) ABSTRACT

A method for treating cirrhosis in a patient in need thereof comprises administering botulinum toxin to the patient. The botulinum toxin may be administered by subcutaneous or intradermal injection. The subcutaneous or intradermal injection may be administered to and/or around the vicinity of a trigeminal nerve, a cervical nerve, a thoracic nerve, a lumbar nerve, a sacral nerve, or a combination thereof of the patient.

19 Claims, No Drawings

(56) References Cited

OTHER PUBLICATIONS

Donald C. Rojas, "The role of glutamate and its receptors in autism and the use of glutamate receptor antagonists in treatment", J Neural Transm. Aug. 2014 ; 121(8): 891-905, pp. 1-24

Juan M. Espinosa-Sanchez et al, "New insights into pathophysiology of vestibular migraine", Frontiers in Neurology, Feb. 2015 l vol. 6 l Article 12, pp. 1-6.

Colleen Doherty, MD, "The Link Between Migraines and Tinnitus, Buzzing or ringing in your ears could be related to your episodes", VeryWell Health, Aug. 6, 2019, pp. 1-13 https://www.verywellhealth.com/link-between-migraines-and-tinnitus-4077631.

K,J. Powell et aL, "The Role of CGRP in the Development of Morphine Tolerance and Physical Dependence", 4th International Meeting on Calcitonin Gene-Related Peptide (CGRP), The ScientificWorld (2001) 1 (51), 21. 2 pages.

Vacca et al., "Botulinum Toxin A Increases Analgesic Effects of Morphine, Counters Development of Morphine Tolerance and Modulates Glia Activation and μ Opioid Receptor Expression in Neuropathic Mice", Brain, Behavior, Immunity 32 (2013), pp. 40-50 (Year: 2013).

Mayo clinic article, "Autism Spectrum Disorder", Symptoms and Causes, 5 pages (Year: 2019) downloaded on Dec. 23, 2019 from: https://www.mayoclinic.org/diseases-conditions/autism-spectrum-disorder/ symptoms-causes/ syc-20352928?p=1.

The Machine Translation of WO2010013495, English Abstract,"Pharmaceutical Composition Containing Highly Purified Botulinum Neurotoxin Therapeutic Agent As Active Ingredient, and Use Thereof", Akaike et al.; Feb. 4, 2010 (Year: 2010).

Nair et al., "Impaired Thalamocortical Connectivity in Autism Spectrum Disorder: A Study of Functional and Anatomical Connectivity", Brain, Journal of Neurology, 2013; 136: 1942-1955 (Year: 2013).

Panju et al., "Atypical Sympathetic Arousal in Children With Autism Spectrum Disorder and Its Association With Anxiety Symptomatology", Molecular Autism (2015) 6:64, pp. 1-10 (Year: 2015).

Saunte et al., "Improvement in Reading Symptoms Following Botulinwn Toxin A Injection for Convergence Insufficiency Type Intermittent Exotropia", Acta Ophthalmologica (1755375X). Aug. 2015, vol. 93 Issue 5, pp. 1-3 (Year: 2015).

The WebMD website, "Treatments for Dyslexia", The International Dyslexia Association. National Center for Learning Disabilities. National Center for Neurological Disorders and Stroke, https://www.webmd.com/children/dyslexia-treatments; accessed Jun. 22, 2020 , 1 page, (Year: 2020).

Hulme et al., "Reading Disorders and Dyslexia", Current Opinion Pediatr ics2016, 28: pp. 731-735 (Year: 2016) www.co-pediatrics.com.

Mazzone et al., "Vaginal Afferent Innervation of the Airways in Health and Disease", Physiol Rev 96: 975-1024, 2016, pp. 975-1024, (Year: 2016).

Schematic of innervation of organs, available from https://ars.els-cdn.com/content/image/3-s2.0-B9780323378048000055-f005-001-9780323378048.jpg, downloaded Jun. 22, 2020 and reproduced within the Office action (Year: 2020).

Harvard the Harvard Medical School , "Cardiac Arrhythmias", Harvard Health Publishing, Published Feb. 2019, website; downloaded Jul. 18, 2020 from: https://www.health.harvard.edu/a_to_z/cardiac-arrhythmias-a-to-z; 5 pages total (Year: 2020).

Machine English Translation of the foreign patent document, KR20100032982, 7 pages total (Year: 2010).

Mitchell and Borasio et al., "Amyotrophic Lateral Sclerosis", Seminar, Lancet 2007; vol. 369: 12 pp. 2031-2041 (Year: 2007).

Oomens and Forouzanfare t al., "Pharmaceutical Management of Trigeminal Neuralgia in the Elderly", Review Article Drugs Aging (2015) 32: pp. 717-726 (Year: 2015).

Lewitt and Trosch, et al., "Idiosyncratic Adverse Reactions to Intramuscular Botulinum Toxin Type A Injection", Movement Disorders, 1997; 12: pp. 1064-1067 (Year: 1997).

Squires et al., "The Use of Botulinum Toxin Injections to Manage Drooling in Amyotrophic Lateral Sclerosis/Motor Neurone Disease: A Systematic Review", Dysphagia (2014) 29: pp. 500-508 (Year: 2014)

The website downloaded on Jul. 2, 2020 from Juvenile Amyotrophio Lateral Sclerosis,Genetic and Rare Diseases Information Center (GARD)—an NCATS Program, https://rarediseases.info.nih.gov/diseases/11901/juvenile-amyotrophic-lateral-sclerosis; Jul. 2, 2020, 8 pages total (Year: 2020).

Frank CT Smith, "Hyperhidrosis", Vascular Surgery—II, 2013; 31: pp. 251-255; doi: https://doi.org/10.1016/j.mpsur.2013.03.005 (Year: 2015)

International Search Report and Written Opinion, PCT/US2020/056206, dated Feb. 1, 2021.

Dobrek and Thor, "Glutamate NMDA Receptors in Pathophysiology and Pharmacotherapy of Selected Nervous System Dseases", Postepy Hig Med Dosw (online), 2011; 65: pp. 338-346 , 1 Year: 2011).

Erle CH Lim, "Botulinum toxin, Quo Vadis?", Elsevier Ltd., Medical Hypotheses (2007) 69, pp. 718-723 (Year: 2007) http://inti.elsevierhealth.com/ journals/ mehy.

Web Article, The image downloaded Dec. 4, 2020 from https://nursing-skills.blogspot.com/2014/01/angle-of-injection.html; image reproduced in Office action (Year: 2020.

WebMD, ADHD and Dyslexia: How to Tell Them Apart, Dyslexia and ADHD Similarities and Differences, Nov. 30, 2020, 3 pages, The article downloaded Nov. 30, 2020 from https://www.webmd.com/add-adhd/adhd-dyslexia-tell-apart? print=true; 3 pages total (Year: 2020) WebMD.

Chien et al., "Sympathetic Fiber Sprouting in Chronically Compressed Dorsal Root Ganglia Without Peripheral Axotomy", NIH Public Access, Author Manuscript of J. Neuropathic Pain Symptom Palliation. 2005; 1 (1 ): pp. 19-23 (Year: 2005).

Scott and Fryer, "Role of Parasympathetic Nerves and Muscarinic Receptors in Allergy and Asthma", NIH Public Access, Author Manuscript of Chem Immunol Allergy. 2012; 98: pp. 48-69 (Year: 2012).

* cited by examiner

TREATMENT OF CIRRHOSIS USING BOTULINUM TOXIN

This application is a continuation-in-part of U.S. patent application Ser. No. 16/657,933 and U.S. patent application Ser. No. 16/657,950, filed Oct. 18, 2019, respectively. The entirety of each prior application is expressly incorporated herein by reference thereto.

FIELD OF THE INVENTION

The present invention generally relates to methods for diagnosing and treating (including alleviating and/or preventing) cirrhosis and improving the cirrhosis symptoms of children and adults.

BACKGROUND OF THE INVENTION

Botulinum Toxin

Botulinum toxins cleave and destroy a protein called synaptosomal nerve-associated protein 25 ("SNAP25") and/or synaptobrevin (also called vesicle-associated membrane protein ["VAMP"]). Botulinum toxins A, C, and E cleave SNAP25 at different locations, but the effect is in general the same—the protein is destroyed and cannot function until the cell makes new ones. Botulinum toxins B, D, F and G cleave VAMP present at the cytoplasmic surface of the synaptic vesicle. The two important locations in the body where the proteins are found are at the terminals of the motor neurons (muscle) and in the cell membranes of astrocytes, glial cells, and satellite cells. These three cell types surround sensory neurons and form part of the blood-brain barrier. In motor nerves, to cause them to fire, vesicles of acetylcholine move from inside the motor neuron across the cell membrane at the synapse between the motor nerve and muscle fiber. Acetylcholine is released into the synapse and activates receptors in the muscle fiber, which contracts the muscle fiber. In sensory nerves, when a nerve is damaged from physical or mental injuries, the three aforementioned structural cells produce large amounts of Substance P, Calcitonin Gene Related Peptide (CGRP), and glutamate internally and the molecules are moved by vesicles to the cell membrane where the SNAP25 and/or VAMP moves the molecules through the cell membrane and releases the molecules into the cerebrospinal fluid that surrounds the neurons. There, the molecules bind to the receptor on the sensory nerves, causing the neuroexcitatory effects. The molecules can also diffuse in the cerebral spinal fluid (CSF) and influence other sensory nerves to become hyperactive, a process called central sensitization.

This mechanism of cleaving the SNAP25 and/or VAMP in muscles and sensory nerves causes the only known clinical effects of botulinum, which paralyzes muscles in the motor system for 3-4 months until the cell grows a new protein. This effect has been used for decades for overactive muscles (such as to treat overactive muscles as part of cervical dystonia, blepharospasm, tic, Parkinson's, cerebral palsy, etc.), wrinkles in the face, excessive sweating, and overactive bladder.

In the sensory nerves, the mechanism has been used for migraines and depression. The effect of blocking the SNAP25 and/or VAMP in the glial, satellite, and astrocyte cells will work for 5-9 months until these cells grow new proteins. The important part of this mechanism is that the botulinum effect does not destroy cells and does not stop the normal production of or effects of acetylcholine (muscles) or Substance P, CGRP, or glutamate in sensory nerves. These facts give huge advantages over a monoclonal antibody which would eliminate all glutamate, CGRP, and Substance P. Side effects of such elimination would be disastrous. The receptor antagonists also have problems—for example, because the receptor antagonists are not site-specific, they block glutamate, Substance P, and CGRP everywhere. Too little glutamate, Substance P, and CGRP is a problem, as well as too much. It is difficult to regulate oral or I.V. doses to obtain the correct level of reduction in areas that are too high in glutamate, Substance P, and/or CGRP without over-reduction in areas with normal levels.

Small doses of botulinum toxin injected into a specific muscle can cleave SNAP25 and/VAMP to calm the muscle's overreaction or paralyze the muscle temporarily if desired. Or, if injected subcutaneously near unmyelinated sensory nerves, the botulinum toxin can stop the overproduction of the sensory neuroexcitatory compounds without affecting normal glutamate, Substance P, and CGRP production and function. It is, however, noted that botulinum toxin is highly lethal. Botulinum toxin is the most toxic poison known. One molecule of botulinum toxin destroys one protein molecule of SNAP25 and/or VAMP. A little bit goes a long way. Its production, storage and injection must be done with knowledge and care.

In particular, the mechanism of the sensory effect (stopping overproduction of glutamate, Substance P, and CGRP) is as follows: almost all nerves in the human body are surrounded by a protective coating called myelin, which protects the nerve and makes neural conduction faster. Botulinum toxin has difficulty penetrating the myelin. Just under the skin are sensory pain nerves called C-fibers, which are unmyelinated. Research has shown that very low dose botulinum toxin can penetrate these axons and diffuse up the axon to the cell body into the CSF and affect the SNAP25 and/or VAMP on the glial, satellite, and astrocyte cells. Subsequently, botulinum toxin destroys the SNAP25 and/or VAMP and prevents the release of the excess Substance P, CGRP, and glutamate, which is involved in a response mechanism to neural-injury without affecting normal glutamate, Substance P, and CGRP production, use, or receptors. An example of a malfunction with the normal nerve mechanism is an infection of a nerve by the shingles virus. The infection by the shingles virus damages the nerve but does not kill it, or there would be no feeling (numbness). This causes a spike in the production of glutamate, Substance P, and CGRP. This causes the well-known shingles pain and hypersensitivity. Over a 2-3 month period, the infection is controlled, the nerve heals, and the overproduction of the neuroexcitatory chemicals gets back to normal. However, sometimes for unknown reasons, the overproduction does not get back to normal but remains high, and severe chronic pain and hypersensitivity persists. Chronically overstimulated neurons can cause numerous problems depending on where the neurons are located. The neuroexcitatory chemicals can travel up the spinal cord to the brain in the CSF and affect neurons there. This process is called central sensitization. Depending on where glutamate, Substance P, and CGRP are produced and where the molecules travel to, the molecules can cause chronic pain, headaches, vertigo, sensitivity to light, sensitivity to touch, cold sensitivity, overactive bladder, depression, anxiety, flashbacks, mental fogginess, vasoconstriction of extremities, sleep disturbances, and perhaps the death and malformation of the developing neural architecture in children with ASD (autism).

Liver and Cirrhosis

The liver is an organ found in vertebrates which detoxifies various metabolites, synthesizes proteins, and produces biochemicals necessary for digestion and growth. Located in the abdomen just below the diaphragm, its other roles in metabolism include regulation of glycogen storage, decomposition of red blood cells, and the production of hormones. It produces bile, and an alkaline compound which aids in the breakdown of fat.

The gallbladder, a small pouch that sits just under the liver, stores bile produced by the liver, which is afterwards moved to the small intestine to complete digestion. The liver's highly specialized tissue consisting of mostly hepatocytes regulates a wide variety of high-volume biochemical reactions, including the synthesis and breakdown of small and complex molecules, many of which are necessary for normal vital functions. Estimates regarding the organ's total number of functions vary, but textbooks generally cite it being around 500.

Hepatitis is inflammation of the liver, which can be caused by the overuse of alcohol, a fatty liver, or hepatic viruses A, B, C, and D. Alcoholic hepatitis is caused by the intake of excessive amounts of alcohol, often over long periods of time. Those at high risk may consume 8-10 drinks per day. Alcoholic hepatitis is found in association with fatty liver, an early stage of alcoholic liver disease, which may lead to fibrosis and eventually cirrhosis. Signs and symptoms include jaundice (yellowing of the skin or eyes), ascites (fluid buildup in the abdominal cavity), fatigue from loss of nutrients, minerals, and vitamins, and hepatic encephalopathy (brain dysfunction due to liver failure). Severe cases have a high risk of death but may be treated with glucocorticoids. Alcoholic hepatitis is characterized by a number of symptoms, which may include feeling unwell, enlargement of the liver, ascites, and modest evaluation of liver enzyme levels (as determined by liver function tests). Alcoholic hepatitis may also present with hepatic encephalopathy (brain dysfunction due to liver failure causing symptoms such as confusion, decreased levels of consciousness, or asterixis [a characteristic jerking of the limbs]). Other symptoms may include pale stools when stercobilin, a brown pigment, is absent from the stool (stercobilin is derived from bilirubin metabolites produced by the liver), dark urine due to bilirubin in the urine, swelling of the abdomen, ankles, and/or feet if liver fails to produce albumin, bruising and bleeding easily because of the absence of clotting factors, and pain in the upper right quadrant. The mortality rate is 50% within 2 years of onset despite best care. Alcoholic hepatitis is distinct from cirrhosis caused by long-term alcohol consumption. Alcoholic hepatitis can occur in patients with chronic alcoholic liver disease and alcoholic cirrhosis. Alcoholic hepatitis by itself does not lead to cirrhosis, but cirrhosis is more common in patients with long term alcohol consumption. Some alcoholics develop acute hepatitis as an inflammatory reaction to the cells affected by fatty change. Acute hepatitis is not directly related to the dose of the alcohol. Some people seem more prone to this reaction than others. This inflammatory reaction to the fatty change is called alcoholic steatonecrosis and the inflammation probably predisposes to liver fibrosis.

The osmolality of mammalian extracellular fluid (ECF) is modulated by an osmosensing system located throughout a number of organ systems. This system balances salt and water intake or excretion by signaling the brain. The liver contains receptors for monitoring body fluid homeostasis by detecting key physiological ions (e.g., Na+) present in the portal blood system.

Glucose sensing is known to occur in different cell types and areas of the brain. In the central nervous system, cells expressing glucose transporters (glut), such as neurons and glial cells, are triggered during hypoglycemic conditions to stimulate processes such as glucagon release. Peripherally located glucose sensors are located in, for example, taste buds, intestines, the carotid body, and liver areas. A number of studies have demonstrated glucose sensing by the liver. While the relative contribution of both autonomic arms (sympathetic and parasympathetic) remains to be fully elucidated, both have been demonstrated to play a role in in glucose sensing by the liver. Decreased portal glucose concentrations activate vagal afferent activity, triggering increased food intake. This mechanism appears to be critical before the initiation of food intake, rather than the termination of feeding upon its inhibition.

Afferent fibers in the liver are responsible for a negative feedback loop involving feedback behavior, and alterations in glucose production. Studies performed to differentiate the effects of general abdominal and hepatic vagotomy have suggested that vagal afferent fibers detect the levels of free fatty acids (FFA) in the liver and play a role in feeding behavior. Infusion of linoleic acid, liposyn II, corn oil, or caprylic acid into the portal vein resulted in vagal afferent stimulation from the liver. The vagal response turned out to be the strongest in response to linoleic or triglycerides. In addition, animals fed a diet high in fat displayed a negative feedback behavior, which is blocked by vagotomy of the common hepatic branch. Another study confirmed that these effects were mediated through afferent signaling and not efferent signaling by damage induced to the afferent fibers by exposure to capsaicin. These studies emphasize a role for a reflexive decrease in feeding associated with activation of hepatic afferent fibers. These studies also emphasize that activation of afferent neurons is crucial for directing fat deposition and regulating plasma metabolite levels.

Perhaps even more important than the reflective role of hepatic lipid sensing are its effects on insulin resistance. The lipid sensing of liver directly conflicts with that of the GI tract and the brain in that it reduces the inhibitory actions of insulin on gluconeogenesis, and/or glucose production by the liver. Under normal physiological conditions, a mutually balancing circuit triggered by lipids regulating glucogenesis exists in which the brain/GI tract are in opposition to the liver. Lipid sensing by the brain indirectly inhibits glucose productions, whereas lipid sensing by the liver increases insulin resistance. In disease states characterized by insulin resistance such as diabetes type 2, this balance becomes offset. Here, lipids sensed by the liver increase insulin resistance in obesity-associated diabetes, which contributes to disease pathology. There is a critical need to develop new strategies to delineate the relative roles of the liver and other organs in the initiation of insulin resistance and the resultant diabetic pathology.

Those with alcoholic hepatitis may feel unwell, experience enlargement of the liver, ascites, and have elevation of liver enzyme tests. This type of hepatitis may occur in ⅓ of chronic alcohol drinkers, and 10-20% of these patients progress to alcoholic liver cirrhosis every year. If untreated, mortality can be as high as 40-50% in two years. The best management options are abstinence from alcohol, nutrition supplementation (with added protein and calories), corticosteroids, pentoxyifylline, IV N-acetylcysteine, and/or ultimately liver transplantation.

The liver is the only human internal organ capable of natural regeneration of lost tissues—as little as 25% of a donor liver can regenerate into a whole liver. This is, however, not true regeneration but rather compensatory growth in mammals. For those with irreversible liver failure, liver transplantation is the only option. Most transplants have been done for chronic liver diseases leading to cirrhosis, such as chronic hepatitis C, alcoholism, and autoimmune hepatitis.

The liver's nervous system contains both afferent and efferent neurons involved in a number of processes. The afferent arm includes the sensation of lipids, glucose, and metabolites, and triggers the nervous system to make appropriate physiological changes. The efferent arm is essential for metabolic regulation, modulation of fibrosis, and biliary function, among other processes. Branches of both the vagal and splanchnic nerves innervate the liver via the portal area. The sympathetic innervation is postganglionic and originates in the celiac and superior mesenteric ganglia that receive preganglionic fibers from the intermediolateral column of the spinal cord (t-7-t-12). The parasympathetic nerves branch off the vagus nerve and are thought to innervate the liver directly as preganglionic fibers originating in the dorsal motor nucleus of the brainstem, or synapses on ganglia located at the hepatic hilus and within hilar spaces.

Sympathetic release of adrenaline and Substance P causes contraction of the liver sinusoids, whereas parasympathetic release of acetylcholine and vasoactive intestinal peptide (VIP) causes relaxation. Autonomic regulation of the sinusoids may also assist in hepatic blood flow during chronic liver diseases such as fibrosis/cirrhosis. While further research is needed, nitric oxide (NO) and the decreased density of neurons in the sinusoids may determine whether modulation of this pathway would be beneficial for patients. The sympathetic nervous system's intimate relationship with hepatic stellate cells (HSC) and hepatic oval cells (HOC) makes it a candidate for augmenting liver repair. In the normal liver, both HSC and HOC are in a quiescent state but are activated during liver damage. HSC are the fibrogenic cells of the liver that take on a myofibroblastic phenotype during repair characterized by proliferation, synthesis of matrix proteins, and expression of a-smooth muscle actin. There is indication the sympathetic nervous system inhibits HOC and activates HSC. Inhibitors of the sympathetic nervous system are potential drug targets for the treatment of cirrhosis. More research into the basic mechanisms of the liver's sympathetic activity during fibrogenesis will be important.

The autonomic nervous system of the liver plays a key role in the maintenance of homeostasis and other processes. It contains receptors for glucose and lipids that trigger a negative feedback system to modify physiological responses such as satiety and metabolism. Recent advances have touched on the importance of the liver in metabolism, and regulation of insulin and glucagon. Since obesity and diabetes are prevalent in the U.S., it is necessary to understand the mechanisms whereby the liver controls metabolism and feeding. The studies reviewed in this work suggested that glucose and energy homeostasis were highly affected by the hepatic nervous system. These processes are potential drug targets for clinical practice. With the increasing number of individuals affected by liver fibrosis, the role of the autonomic nervous system in liver regeneration is HSC, Kupffer cells, HOC, and inflammatory cells. It would be of immense importance to learn how these cells are innervated, as it could hold clinical importance. Future research should be directed toward an understanding of the neurotransmitters, signaling molecules, and cell types innervated by the hepatic nervous system.

SUMMARY OF THE INVENTION

The claimed invention is related to methods for treating cirrhosis in a patient in need thereof. The method comprises administering botulinum toxin to the patient. The botulinum toxin may be administered by subcutaneous or intradermal injection. The subcutaneous or intradermal injection may be administered to and/or around the vicinity of a trigeminal nerve of the patient. The selected trigeminal nerve comprises an ophthalmic nerve, maxillary nerve, mandibular nerve, supraorbital nerve, supratrochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, a greater occipital nerve, or a combination thereof. The subcutaneous or intradermal injection may be administered to and/or around the vicinity of a cervical nerve of the patient. The selected cervical nerve comprises the c-2 nerve, c-3 nerve, c-4 nerve, c-5 nerve, c-6 nerve, c-7 nerve, c-8 nerve, or a combination thereof. The subcutaneous or intradermal injection may be administered by subcutaneous or intradermal injection to and/or around a vicinity of a thoracic nerve of the patient. The selected thoracic nerve comprises the t-2 nerve, t-3 nerve, t-5 nerve, t-6 nerve, t-7 nerve, t-8 nerve, t-9 nerve, t-10 nerve, t-11 nerve, t-12 nerve, or a combination thereof. The subcutaneous or intradermal injection may be administered to and/or around the vicinity of a lumbar nerve of the patient. The selected lumbar nerve comprises the 1-1 nerve, 1-2 nerve, 1-3 nerve, 1-4 nerve, 1-5 nerve, or a combination thereof. The subcutaneous or intradermal injection may be administered to and/or around the vicinity of a sacral nerve of the patient. The selected sacral nerve comprises the s-1 nerve, s-2 nerve, s-3 nerve, s-4 nerve, s-5 nerve, or a combination thereof. In some embodiments, the subcutaneous or intradermal injection may be administered to and/or around the vicinity of a trigeminal nerve, a cervical nerve, a thoracic nerve, a lumbar nerve, and a sacral nerve of the patient. Preferably, the administering for an adult who weighs about 150 lbs. comprises by subcutaneous or intradermal injection 2-4 units to and/or around the vicinity of an ophthalmic, maxillary, and/or mandibular nerve of the trigeminal nerve (bilateral), 2-4 units to and/or around the vicinity of the c-2 to c-3, c-4 to c-6, and/or c-7 to c-8 of the cervical nerve, about one-inch lateral to the patient's spine (bilateral), 2-4 units to and/or around the vicinity of the t-2 to t-3, t-5 to t-6, t-7 to t-9, and/or t-10 to t-12 of the thoracic nerve, about one inch lateral to the patient's spine (bilateral), 2-4 unit to and/or around the vicinity of the 1-1 to 1-2,1-2 to 1-3, and/or 1-4 to 1-5 of the lumbar nerve, about one inch lateral to the patient's spine (bilateral), and/or 2-4 units to and/or around the vicinity of the s-1 to s-2, s-3 to s-4, and/or s-4 to s-5 of the sacral nerve, about one inch lateral to the patient's spine (bilateral). In some desired embodiments, the botulinum toxin comprises botulinum toxin type A, botulinum toxin type B, botulinum toxin type C, botulinum toxin type D, botulinum toxin type E, botulinum toxin type F, botulinum toxin type G, a fragment thereof, a hybrid thereof, a chimera thereof, or a combination thereof. In further embodiments, a total dosage of the botulinum toxin for an adult who weighs about 150 lbs is between about 1 unit and about 150 units. The dosage of botulinum toxin for an adult or a child is adjusted for age, weight, or a combination thereof.

DETAILED DESCRIPTION OF THE PREFERRED EMBODIMENTS

Further in relation to this, before explaining at least the preferred embodiments of the invention in greater detail, it is to be understood that the invention is not limited in its application to the details of construction and to the arrangements of the components set forth in the following description. It would be understood by those of ordinary skill in the art that embodiments beyond those described herein are contemplated, and the embodiments can be practiced and carried out in a plurality of different ways. Also, it is to be understood that the terminology used herein is for the purpose of description and should not be regarded as a limiting factor.

Unless otherwise defined, the terms used herein refer to that which the ordinary artisan would understand such term to mean based on the contextual use of such term herein. To the extent that the meaning of a term used herein as understood by the ordinary artisan based on the contextual use of such term differs in any way from any particular dictionary definition of such term, it is intended that the meaning of the term as understood by the ordinary artisan will prevail.

As used herein, the term "about" means approximately or nearly and in the context of a numerical value or range set forth herein means 10% of the numerical value or range recited or claimed.

The term "treating" includes delaying, alleviating, mitigating or reducing the intensity, progression, or worsening of one or more attendant symptoms of a disorder or condition and/or alleviating, mitigating or impeding one or more causes of a disorder or condition. Treatment under the claimed invention may be a preventative treatment, prophylactic treatment, remission of treating or ameliorating treatment.

The term "therapeutically effective amount" or "therapeutically effective dose" refers to the amount of a composition, compound, therapy, or course of treatment that, when administered to an individual for treating a disorder or disease, is sufficient to effect such treatment for the disorder or disease. The "therapeutically effective amount" will vary depending on the composition, the compound, the therapy, the course of treatment, the disorder or disease and its severity and the age, weight, etc., of the individual to be treated.

The term "unit" refers to the amount of botulinum toxin needed to kill 50% of a group of 18-20 gm female Swiss-Webster mice given the injection intraperitoneally.

The term "vicinity of a nerve" refers to anywhere on the dermatome involved with the nerve.

In accordance with the principles of the present invention, use of botulinum toxin to treat cirrhosis is provided.

Treatment of Cirrhosis

Cirrhosis, also known as liver cirrhosis or hepatic cirrhosis, is a condition in which the liver does not function properly due to long-term damage. This damage is characterized by the replacement of normal liver tissue by scar tissue. Typically, the disease develops slowly over months and years. Early on, there is often no symptom. As the disease worsens, the person may become tired, weak, itchy, have swelling in the lower legs, develop yellow skin, bruise easily, have fluid buildup in the abdomen, or develop spider-like blood vessels on the skin. The fluid build-up in the abdomen may become spontaneously infected. Other serious complications include hepatic encephalopathy, bleeding from dilated veins in the esophagus or dilated stomach veins, and liver cancer. Hepatic encephalopathy results in confusion and may lead to unconsciousness.

Cirrhosis is most commonly caused by alcohol, hepatitis B, hepatitis C, and fatty liver disease. Typically, more than two or three alcoholic drinks per day over a number of years is required for alcoholic cirrhosis to occur. Non-alcoholic fatty liver disease has many causes, including being overweight, diabetes, high blood fats, and high blood pressure.

Diagnosis is preferably based on blood testing, medical imaging, and liver biopsy. Some causes of cirrhosis such as hepatitis B can be prevented by vaccination. Hepatitis B and C may be treatable with antiviral medications. Autoimmune hepatitis may be treated with steroid medications. Ursodiol may be useful if the disease is due to blockage of the bile ducts. Other medications may be useful for complications such as abdominal and leg swelling, hepatic encephalopathy, and dilated esophageal veins. In severe cirrhosis, a liver transplant may be an option.

Cirrhosis of the liver is slow and gradual in its development. It is usually well advanced before its symptoms are noticeable enough. Weakness and weight loss may be early symptoms. The following features are direct consequences of the liver cells not functioning: spider angioma, palmar erythema, gynecomastia, hypogonadism, enlarged liver size, ascites, fetor hepaticus, jaundice, splenomegaly, esophageal varices, caput medusa, and Cruveilhier-Baumgarten. In advanced disease, some first signs may be bruising and bleeding, hepatic encephalopathy, acute kidney injury, or etc.

Liver cirrhosis has many possible causes, and sometimes more than one cause is present in the same person. Globally, 57% of cirrhosis is attributable to either hepatitis B (30%) or hepatitis C (27%). Alcohol consumption is another major cause, accounting for about 20% of cases. Liver cirrhosis is generally caused by the following:

a) Alcoholic Liver Disease (ALD): Alcoholic cirrhosis develops for 10-20% of individuals who drink heavily for a decade or more. Alcohol seems to injure the liver by blocking the normal metabolism of proteins, fats, and carbohydrates. This injury happens through the formation of acetaldehyde from alcohol which itself is reactive, but which also leads to the accumulation of other active products in the liver. Patients may also have concurrent alcoholic hepatitis with fever, hepatomegaly, jaundice, and anorexia. AST and ALT blood levels are both elevated, but at less than 300 IU/liter, with an AST:ALT ratio>2.0, a value rarely seen in other liver diseases. In the U.S., 40% of cirrhosis-related deaths are due to alcohol.

b) Non-Alcoholic Steatohepatitis (NASH): In NASH, fat builds up in the liver and eventually causes scar tissue. This type of hepatitis appears to be associated with obesity (40% of NASH patients), diabetes, protein malnutrition, coronary artery disease, and treatment with steroid medications. This disorder is similar in its signs to alcoholic liver disease, but the patient does not have an alcohol history. A biopsy is needed for diagnosis.

c) Chronic Hepatitis C: Infection with the hepatitis C virus causes inflammation of the liver and a variable grade of damage to the organ. Over several decades, this inflammation and damage can lead to cirrhosis. Among patients with chronic hepatitis C, 20-30% will develop cirrhosis. Cirrhosis caused by hepatitis C and alcoholic liver disease are the most common reasons for liver transplant.

d) Chronic Hepatitis B: The hepatitis B virus causes liver inflammation and injury that over several decades can lead to cirrhosis. Hepatitis D is dependent on the presence of hepatitis B and accelerates cirrhosis in co-infection.

e) Other causes may include, but not be limited to, primary biliary cholangitis, primary sclerosing cholangitis, autoimmune hepatitis, hereditary hemochromatosis, and Wilson's disease.

As the liver is damaged by aforementioned causes, it loses its ability to regenerate itself and areas of the liver start to die and are replaced with fibroid (scar) tissue. This is when hepatitis becomes cirrhosis. In its early stages if the cause can be eliminated, it may be reversible. In moderate to severe cases, the end result is liver transplant or death. There is a 50% death rate in 2 years. This occurs even if the damaging factors are eliminated. What causes some people's damage to progress from hepatitis to cirrhosis and some not to progress? What causes some people's cirrhosis to continue to progress even if the initiating factor is eliminated?

Not wishing to be bound by a theory, the cause of cirrhosis is believed to be the damage that occurs during hepatitis to the sensory nerves in the liver. They are from the spinal nerves t-7-t-12 and the vagus nerve. Neuropathic conditions can develop when sensory nerves are damaged. It has been shown in other neuropathic conditions such as migraines and fibromyalgia. The neuroexcitatory peptides glutamate, Substance P, and CGRP are released from the neurostructural cells and cause hyperfunctioning of the involved nerves. In cirrhosis, levels of Substance P and CGRP (and to a lesser degree glutamate) are elevated in the liver and blood. Like migraines and fibromyalgia, sometimes even when the initiating factor is eliminated, the nerves continue to overproduce Substance P, CGRP, and glutamate. These excitatory cytokines disrupt the regenerative ability of the liver and lead to hepatic cell death and replacement of the dead tissue with fibroid tissue. The following is a list of some facts from previous studies:

a) Substance P increases liver fibrosis by differential change in senescence of cholangiocytes and hepatic stellate cells.

b) Plasma Substance P levels increase in cirrhosis by 50%. The worse the cirrhosis, the higher the Substance P levels.

c) In blood, Substance P levels are significantly higher in patients with chronic liver disease (119.5±68.2 pg/ml) compared to people without chronic liver disease (16.2±4.6 pg/ml). This amounts to a 738% increase.

d) Substance P antagonists protect mice from inflammatory liver disease.

e) In blood, Substance P levels are significantly higher in patients with cirrhosis (12.1 pmol/L) compared to people without cirrhosis (6.9 pmol/L). The worse the cirrhosis, the higher the levels were above normal.

f) In mice, the knockout gene for CGRP stops cholestatic liver disease.

g) Plasma levels of Substance P are elevated in patients with nonalcoholic cirrhosis and may play a role in the pathogenesis of spider angiomas.

h) Substance P is thought to be a factor in water excretion disorder in patients with cirrhosis.

i) Cutting the sensory nerves to the liver reduced fibrosis in liver disease.

j) There is a comorbidity between migraines, fibromyalgia, and cirrhosis. They are both known to be caused by the overproduction of glutamate, Substance P, and CGRP.

To diagnose cirrhosis, blood levels of Substance P and CGRP can be checked after a clinical diagnosis of cirrhosis at regular doctor visits. Periodic blood tests for elevated Substance P and CGRP in patients that are at risk of developing cirrhosis, such as chronic alcohol users, hepatitis B or C patients, or obese patients, so they can be diagnosed before the damage becomes too severe.

If a patient is diagnosed to experience cirrhosis, he or she can be given botulinum toxin subcutaneously or by any other injection that allows the botulinum toxin to reach the unmyelinated sensory C fiber (e.g., intradermal injection, etc.) to prevent or alleviate related symptoms and/or blood tests to assess blood levels of Substance P and CGRP. Because the sensory innervation of the lungs and bronchi comes from the vagus nerve and branches of spinal nerves, C1-T4, the botulinum toxin injection can be given to and/or around the vicinity of a trigeminal nerve, a cervical nerve, a thoracic nerve, a lumbar nerve, and/or a sacral nerve of the patient. Preferably, it is not necessary to inject botulinum toxin to the vagus nerve directly because there is numerous anastomosis between the trigeminal nerves and the vagus nerves. The selected trigeminal nerve may include, but is not limited to, an ophthalmic nerve, maxillary nerve, mandibular nerve, supraorbital nerve, supratrochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, a greater occipital nerve, or a combination thereof. In the facial dermatome, botulinum toxin is injected subcutaneously to the trigeminal nerve or around the vicinity of the trigeminal nerve because the trigeminal nerve is entirely sensory. In contrast, the facial nerve supplies motor innervations to the face and has no subcutaneous axons. Thus, injecting botulinum toxin to the trigeminal nerve minimizes or eliminates muscular side effects. The selected cervical nerve may include, but is not limited to, the c-2 nerve, c-3 nerve, c-4 nerve, c-5 nerve, c-6 nerve, c-7 nerve, c-8 nerve, or a combination thereof. The selected thoracic nerve may include, but is not limited to, the t-2 to t-3 nerve, t-5 to t-6 nerve, t-7 to t-9 nerve, and/or t-10 to t-12 nerve, or a combination thereof. The selected lumbar nerve may include, but is not limited to, the 1-1 to 1-2 nerve, 1-2 to 1-3 nerve, and/or 1-4 to 1-5 nerve, or a combination thereof. The selected sacral nerve may include, but is not limited to, the s-1 to s-2, s-3 to s-4, and/or s-4 to s-5, or a combination thereof. For example, 2-4 units to and/or around the vicinity of an ophthalmic, maxillary, and/or mandibular nerve of the trigeminal nerve (bilateral), 2-4 units to and/or around the vicinity of the c-2 to c-3, c-4 to c-6, and/or c-7 to c-8 of the cervical nerve, about one-inch lateral to the patient's spine (bilateral), 2-4 units to and/or around the vicinity of the t-2 to t-3, t-5 to t-6, t-7 to t-9, and/or t-10 to t-12 of the thoracic nerve, about one inch lateral to the patient's spine (bilateral), 2-4 unit to and/or around the vicinity of the 1-1 to 1-2,1-2 to 1-3, and/or 1-4 to 1-5 of the lumbar nerve, about one inch lateral to the patient's spine (bilateral), and/or 2-4 units to and/or around the vicinity of the s-1 to s-2, s-3 to s-4, and/or s-4 to s-5 of the sacral nerve, about one inch lateral to the patient's spine (bilateral) can be administered. In a particular embodiment, 2 units in ophthalmic, 2 units in maxillary, 2 units in mandibular of trigeminal nerve bilaterally; 2 units in the c-2-c-3, 2 units in the c-5-c-6, 2 units in the c-7-c-8 of cervical nerve bilaterally; 2 units in the t-1-t-3, 2 units in the t-5-t-6, 2 units in the t-8-t-9, 2 units in the t-11-t-12 of thoracic nerve bilaterally; 2 units in the 1-1-1-2, 2 units in the 1-3-1-4, 2 units in the 1-4-1-5 of lumbar nerve bilaterally; 2 units in the s-1-s-2, 2 units in the s-3-s-4, 2 units in the s-5-s-6 of sacral nerve bilaterally for a total of 64 units can be administered. While the administration site is about one-inch lateral to the patient's spine in the above embodiment, the distance can be more than 0 inches, about 0.1-3 inches, about 0.5-2.5 inches or about 1.0-2.0 inches. Alternatively, the distance can be about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0 inches. The methods according to embodiments of the present invention are preferably applied to all or many of these locations. Depending on symptoms or conditions, the botulinum toxin used in embodiments of the present invention can be injected to a subset or subgroup of the locations described in embodiments of the present invention. In one embodiment, 3 injections of 2 units each distributed along each side of the neck in the cervical area on the trigeminal nerve, 1 injection of 2 units in the ophthalmic, maxillary, mandibular division subcutaneously and bilaterally. These dosages are for an adult who weighs about 150 lbs. The dosage for an adult or a child with cirrhosis would have to be adjusted for age, weight, or a combination thereof.

The methods according to embodiments of the present invention are novel and inventive as they allow for a minimal amount of botulinum toxin to be injected and still cover all dermatomes with no or minimal motor involvement. By using a subcutaneous or intradermal injection that reaches the unmyelinated C-fibers, it takes a lot less botulinum toxin to absorbed into them as opposed to the myelinated nerves, and there are no motor nerves in the epithelium. Also, the injection at, for example, ½ to 1 inch from the patient's spine allows for a lower dose of botulinum toxin because there is a shorter distance to the dorsal root ganglia (approximately ¼ inch) for botulinum toxin to diffuse as compared to several feet if given in the arm or leg. The site is the only place in the body where the sensory and motor nerves are not in close proximity. This combination of low dose and separation of approximately 1 inch of bone and tissue between the motor and sensory nerves should minimize or eliminate any motor side effects. Furthermore, the methods according to embodiments of the present invention does not require vagus nerve injection. The only superficial exposure of the vagus nerve is Arnold's nerve which is in the ear canal. It is a mixed motor and sensory nerve, and the motor component of it innervates the throat. If you inject botulinum toxin to or around the Arnold's nerve, you can generate speech and shallowing problems. The inventor(s) have found that there is enough anastomosis between the sensory cervical nerves, the trigeminal nerve and the vagus nerve that botulinum toxin can reach the vagus ganglia and stop the overproduction of Substance P, glutamate, and CGRP.

Botulinum toxin is given to lower the levels of Substance P and CGRP to normal levels, and botulinum toxin normally begins to work after about three days, when injected about ½ to an inch from the spinal cord for all spinal injections. Blood tests to monitor liver function and Substance P and CGRP levels can be done to make sure that the levels drop to normal, and the cirrhosis symptoms can be monitored to make sure the symptoms normalize as well. When the botulinum toxin wears off and blood tests show an increase in Substance P or CGRP and/or the symptoms begins to re-develop, more botulinum toxin can be given by injection to combat this effect. If levels/symptoms fail to normalize, then perhaps a small dose of one of the Substance P and CGRP antagonists can be administered to help lower Substance P and CGRP blood levels to normal without producing motor side effects. For patients, as discussed, it is possible to use the claimed method to delay, alleviate, mitigate or reduce the intensity, progression, or worsening of one or more attendant symptoms of a disorder or condition, and/or the claimed method alleviates, mitigates or impedes one or more causes of a disorder or condition.

In general, the therapeutically effective dosage or amount can be, for example, 1-150 units depending on the patient's body weight. The dosage for adults is, for example, about 1-150 units. For an adult or a child, the dosage can be adjusted to the patient's body weight, age, or a combination thereof. For toddlers (e.g., from about 1 to 5 years old), the dosage can be, for example, about 1-30 units and can be adjusted to the patient's body weight and age. This is an estimate, but 30 units is the maximum dosage that has been used safely since the 1990s in cerebral palsy infants and young children to control their severe muscle spasms.

Botulinum toxin is given to lower the levels of Substance P and CGRP, and botulinum toxin normally begins to work after about three days. It normally takes the botulinum toxin about one to two weeks to reach the height of its effectiveness. Blood levels of Substance P and CGRP can be monitored to make sure that the levels drop to normal, and the patient's physical symptoms can be monitored to make sure the levels normalize as well. When the botulinum toxin wears off and blood tests show an increase in Substance P or CGRP, the symptoms begin to redevelop, more botulinum toxin can be given to combat the symptoms of the condition. If levels/symptoms fail to normalize, then perhaps a small dose of one of the Substance P or CGRP antagonists can be administered to help lower Substance P or CGRP levels without producing side effects. For patients, as discussed, it is possible to use the claimed method to delay, alleviate, mitigate or reduce the intensity, progression, or worsening of one or more attendant symptoms of a disorder or condition, and/or the claimed method alleviates, mitigates or impedes one or more causes of a disorder or condition.

In general, the total dosage can be 1-150 units depending on the patient's body weight. Preferably, the total dosage is about 20-150 units. Preferably, the total dosage for adults whose weight is 150 lbs is about 20-150 units. For children over about 5 years old, after which brain formation has generally ceased, the total dosage can be adjusted to the child's body weight.

Botulinum toxins for use according to the present invention can be stored in lyophilized, vacuum dried form in containers under vacuum pressure or as stable liquids. Prior to lyophilization, the botulinum toxin can be combined with pharmaceutically acceptable excipients, stabilizers and/or carriers, such as albumin. The lyophilized material can be reconstituted with saline or water to create a solution or composition containing the botulinum toxin to be administered to the patient.

Preferably, the botulinum neurotoxin is peripherally administered by administering it to or in the vicinity of the aforementioned nerve or to the aforementioned nerve branch or its ganglion nuclei. This method of administration permits the botulinum neurotoxin to be administered to and/or to affect select intracranial target tissues. Methods of administration include injection of a solution or composition containing the botulinum neurotoxin, as described above, and include implantation of a controlled release system that controllably releases the botulinum neurotoxin to the target trigeminal tissue. Such controlled release systems reduce the need for repeat injections. Diffusion of biological activity of botulinum toxin within a tissue appears to be a function of dose and can be graduated. Jankovic J., et al *Therapy with Botulinum Toxin*, Marcel Dekker, Inc., (1994), page 150. Thus, diffusion of botulinum toxin can be controlled to reduce potentially undesirable side effects that may affect the patient's cognitive abilities. For example, the botulinum neurotoxin may be administered so that the botulinum neurotoxin primarily effects neural systems believed to be involved in a selected neuropsychiatric disorder, and does not have negatively adverse effects on other neural systems.

In addition, the botulinum neurotoxin may be administered to the patient in conjunction with a solution or composition that locally decreases the pH of the target tissue environment. For example, a solution containing hydrochloric acid may be used to locally and temporarily reduce the pH of the target tissue environment to facilitate translocation of the neurotoxin across cell membranes. The reduction in local pH may be desirable when the composition contains fragments of botulinum neurotoxins that may not have a functional targeting moiety (e.g., a portion of the toxin that binds to a neurotoxin receptor), and/or a translocation domain). By way of example, and not by way of limitation, a fragment of botulinum toxin that comprises the proteolytic domain of the toxin may be administered to the patient in conjunction with an agent that decreases the local pH of the target tissue. Without wishing to be bound by any particular theory, it is believed that the lower pH may facilitate the translocation of the proteolytic domain across the cell membrane so that the neurotoxin fragment can exert its effects within the cell. The pH of the target tissue is only temporarily lowered so that neuronal and/or glial injury is reduced.

The botulinum toxin used in the treatment in accordance with embodiments of the present invention comprises botulinum toxin type A, botulinum toxin type B, botulinum toxin type C, botulinum toxin type D, botulinum toxin type E, botulinum toxin type F, botulinum toxin type G, a fragment thereof, a hybrid thereof, a chimera thereof, or a combination thereof. Because of different mechanisms and cleavage sites of botulinum toxins, the potency, dosage, or duration may vary depend on the type of botulinum toxins. The botulinum toxin can be used with other modulating drugs or chemicals. In further embodiments, the therapeutically effective amount of the botulinum toxin administered is between about 1 unit and about 150 units.

In some embodiments, a composition administered to a patient consists of botulinum toxin(s). Alternatively, a pharmaceutically active composition contained in a composition administered to a patient consists of botulinum toxin(s). The composition may additionally include, but not be limited to, a pharmaceutically inactive excipient, stabilizer and/or carrier. If lyophilized, the botulinum toxin may be reconstituted with saline or water to make a solution or composition to be administered to the patient. Alternatively, a composition administered to a patient comprises botulinum toxin(s) and other pharmaceutically active ingredients.

Unless defined otherwise, all technical and scientific terms used herein have same meaning as commonly understood by the person of ordinary skill in the art to which this invention belongs.

It should be understood that the above description of the invention and specific examples, while indicating preferred embodiments of the present invention, are given by way of illustration and not limitation. Many changes and modifications within the scope of the present invention may be made without departing from the spirit thereof, and the present invention includes all such changes and modifications.

What is claimed is:

1. A method for treating cirrhosis in a patient in need thereof, comprising administering botulinum toxin to the patient, thereby treating cirrhosis, wherein the administering for an adult comprises, by subcutaneous or intradermal injection to a dermatome, injecting 2-4 units to and/or around the vicinity of a trigeminal nerve, 2-4 units to and/or around the vicinity of a cervical nerve, lateral to the patient's spine, 2-4 units to and/or around the vicinity of a thoracic nerve, lateral to the patient's spine, 2-4 units to and/or around the vicinity of a lumbar nerve, lateral to the patient's spine, and/or 2-4 units to and/or around the vicinity of a sacral nerve, lateral to the patient's spine.

2. The method of claim 1, wherein the trigeminal nerve comprises an ophthalmic nerve, maxillary nerve, mandibular nerve, supraorbital nerve, supratrochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, a greater occipital nerve, or a combination thereof.

3. The method of claim 1, wherein the cervical nerve comprises a c-2 nerve, c-3 nerve, c-4 nerve, c-5 nerve, c-6 nerve, c-7 nerve, c-8 nerve, or a combination thereof.

4. The method of claim 1, wherein the thoracic nerve comprises a t-2 nerve, t-3 nerve, t-5 nerve, t-6 nerve, t-7 nerve, t-8 nerve, t-9 nerve, t-10 nerve, t-11 nerve, t-12 nerve, or a combination thereof.

5. The method of claim 1, wherein the lumbar nerve comprises an 1-1 nerve, 1-2 nerve, 1-3 nerve, 1-4 nerve, 1-5 nerve, or a combination thereof.

6. The method of claim 1, wherein the sacral nerve comprises an s-1 nerve, s-2 nerve, s-3 nerve, s-4 nerve, s-5 nerve, or a combination thereof.

7. The method of claim 1, wherein the botulinum toxin comprises botulinum toxin type A, botulinum toxin type B, botulinum toxin type C, botulinum toxin type D, botulinum toxin type E, botulinum toxin type F and botulinum toxin type G, a fragment thereof, a hybrid thereof, a chimera thereof, or a combination thereof.

8. The method of claim 1, wherein each of the subcutaneous or intradermal injection is bilateral.

9. The method of claim 1, wherein a total dosage of the botulinum toxin for an adult who weighs about 150 lbs is between about 2 and about 150 units.

10. The method of claim 1, wherein a total dosage of the botulinum toxin for an adult or a child is adjusted for age, weight, or a combination thereof.

11. A method for treating cirrhosis in a patient in need thereof, comprising administering botulinum toxin to the patient, thereby alleviating, mitigating or impeding one or more causes of cirrhosis, wherein the administering for an adult comprises, by subcutaneous or intradermal injection to a dermatome, injecting 2-4 units to and/or around the vicinity of a trigeminal nerve, 2-4 units to and/or around the vicinity of a cervical nerve, lateral to the patient's spine, 2-4 units to and/or around the vicinity of a thoracic nerve, lateral to the patient's spine, 2-4 units to and/or around the vicinity of a lumbar nerve, lateral to the patient's spine, and/or 2-4 units to and/or around the vicinity of a sacral nerve, lateral to the patient's spine,
    wherein a total dosage of the botulinum toxin for an adult who weighs about 150 lbs is less than or equal to about 65 units, and
    wherein a total dosage of the botulinum toxin for an adult or a child is adjusted for age, weight, or a combination thereof.

12. The method of claim 11, wherein the trigeminal nerve comprises an ophthalmic nerve, maxillary nerve, mandibular nerve, supraorbital nerve, supratrochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, a greater occipital nerve, or a combination thereof.

13. The method of claim 11, wherein the cervical nerve comprises a c-2 nerve, c-3 nerve, c-4 nerve, c-5 nerve, c-6 nerve, c-7 nerve, c-8 nerve, or a combination thereof.

14. The method of claim 11, wherein the thoracic nerve comprises a t-2 nerve, t-3 nerve, t-5 nerve, t-6 nerve, t-7 nerve, t-8 nerve, t-9 nerve, t-10 nerve, t-11 nerve, t-12 nerve, or a combination thereof.

15. The method of claim 11, wherein the lumbar nerve comprises an l-1 nerve, l-2 nerve, l-3 nerve, l-4 nerve, l-5 nerve, or a combination thereof.

16. The method of claim 11, wherein the sacral nerve comprises an s-1 nerve, s-2 nerve, s-3 nerve, s-4 nerve, s-5 nerve, or a combination thereof.

17. The method of claim 11, wherein the administered botulinum toxin comprises botulinum toxin type A, botulinum toxin type B, botulinum toxin type C, botulinum toxin type D, botulinum toxin type E, botulinum toxin type F, botulinum toxin type G, a fragment thereof, a hybrid thereof, a chimera thereof, or a combination thereof.

18. The method of claim 11, wherein each of the subcutaneous or intradermal injection is bilateral.

19. A method for treating cirrhosis in a patient in need thereof, comprising administering botulinum toxin to the patient, thereby alleviating, mitigating or impeding one or more causes of cirrhosis,
   wherein the administering for an adult comprises, by subcutaneous or intradermal injection to a dermatome, injecting 2-4 units to and/or around the vicinity of a trigeminal nerve, 2-4 units to and/or around the vicinity of a cervical nerve, lateral to the patient's spine, 2-4 units to and/or around the vicinity of a thoracic nerve, lateral to the patient's spine, 2-4 units to and/or around the vicinity of a lumbar nerve, lateral to the patient's spine, and/or 2-4 units to and/or around the vicinity of a sacral nerve, lateral to the patient's spine.

* * * * *